United States Patent
Lelevé et al.

(10) Patent No.: US 7,860,275 B2
(45) Date of Patent: Dec. 28, 2010

(54) METHOD FOR DETECTING RAIN ON A WINDSCREEN

(75) Inventors: Joël Lelevé, Epinay sur Seine (FR); Julien Rebut, Paris (FR); Abdelaziz Bensrhair, Mont Saint Aignan (FR); Georges Challita, Mont Saint Aignan (FR)

(73) Assignee: Valeo Vision, Bobigny (FR)

( * ) Notice: Subject to any disclaimer, the term of this patent is extended or adjusted under 35 U.S.C. 154(b) by 797 days.

(21) Appl. No.: 11/751,160

(22) Filed: May 21, 2007

(65) Prior Publication Data

US 2007/0267993 A1    Nov. 22, 2007

(30) Foreign Application Priority Data

May 22, 2006   (FR)   .................................. 06 04573

(51) Int. Cl.
*G06K 9/00* (2006.01)
*G01N 21/00* (2006.01)
(52) U.S. Cl. ...................... 382/104; 382/274; 356/239.8
(58) Field of Classification Search ................. 382/103, 382/104, 106, 107, 168, 172, 181, 192–194, 382/199, 232, 240, 255, 274, 276, 286, 305, 382/312; 250/208.1, 227.25; 356/239.8
See application file for complete search history.

(56) References Cited

U.S. PATENT DOCUMENTS

| | | | | |
|---|---|---|---|---|
| 6,392,218 | B1 * | 5/2002 | Kuehnle | 250/208.1 |
| 6,596,978 | B2 * | 7/2003 | Hochstein | 250/208.1 |
| 2005/0168732 | A1 * | 8/2005 | Miller et al. | 356/239.8 |
| 2005/0206511 | A1 | 9/2005 | Heenan et al. | |
| 2006/0163458 | A1 * | 7/2006 | Reime | 250/227.25 |
| 2006/0228001 | A1 * | 10/2006 | Tsukamoto | 382/104 |

FOREIGN PATENT DOCUMENTS

| | | | |
|---|---|---|---|
| EP | 1560159 | A2 | 8/2005 |
| EP | 1580092 | A2 | 9/2005 |
| FR | 2884316 | A1 | 10/2006 |
| WO | 9923828 | A1 | 5/1999 |
| WO | 03097420 | A1 | 11/2003 |
| WO | 2006024247 | A1 | 3/2006 |

\* cited by examiner

*Primary Examiner*—Seyed Azarian
(74) *Attorney, Agent, or Firm*—Jacox, Meckstroth & Jenkins

(57) ABSTRACT

A method for detecting raindrops on a windscreen, which uses a camera, which is fitted inside the vehicle opposite the windscreen and which is focused at infinite. The method comprises steps of acquiring images by a camera through the windscreen, camera preferably focused at infinite, retrieving the contours of the spots present on the acquired images, and realizing the histogram of the widths of contours of the spots.

20 Claims, 2 Drawing Sheets

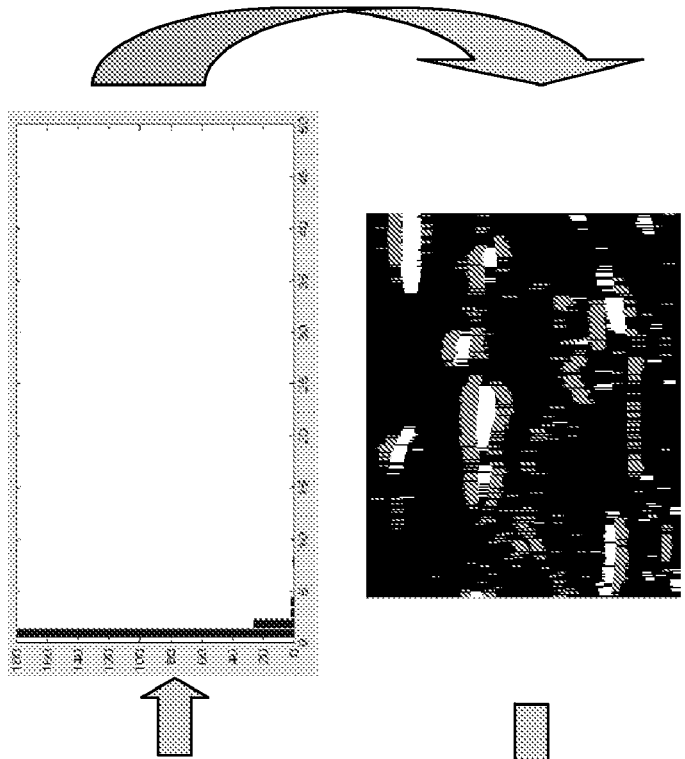
FIG. 3A
FIG. 3B
FIG. 3C
FIG. 3D
FIG. 3E
FIG. 3

METHOD FOR DETECTING RAIN ON A WINDSCREEN

BACKGROUND OF THE INVENTION

1. Field of the Invention

The invention relates in a general way to the field of motor vehicles. More particularly, the invention is interested in the methods for detecting rain on a vehicle windscreen by processing images, particularly in order to trigger the automatic control of a functionality of the vehicle, particularly that of the windscreen wipers.

Image processing techniques aimed at detecting raindrops on a windscreen are already known: they generally require at least one sensor/at least one camera placed inside the vehicle, focused on the windscreen and dedicated to this application. This is the case for example in U.S. Pat. No. 6,596,978, which details a system for detecting raindrops using two dedicated detectors.

One drawback of these techniques is that they have the express need for the detectors to be dedicated to detecting rain, whereas other functionalities also require sensors, to detect an oncoming vehicle or a roadside edge for example. The tendency is to multiply the number of sensors in the vehicle, which increases their total cost, renders the installation of these various sensors more complex, and tends to encumber the vehicle more, particularly its cab interior.

2. Description of Related Art

The object of the invention is therefore to overcome this drawback by proposing an improved method for detecting rain on a windscreen. It concerns more particularly a method which is at least as reliable as the known methods, but which, in particular, deploys more compact and/or less complex and/or easier means of using or mounting on the vehicle.

SUMMARY OF THE INVENTION

The object of the invention first of all is a method for detecting raindrops on a windscreen, which uses a camera fitted inside the vehicle opposite the windscreen and which is focused at infinite.

Advantageously, this camera is also used in the vehicle for other detection functions, more particularly to detect vehicles (so as to make the vehicle headlamps switch from one mode of lighting to another) and/or to detect the roadside edges (so as to send a warning to the driver if he leaves the roadway). It should be noted that the same camera may therefore be used to capture close-up and remote images, having the same optical trajectory, and without a zone of the camera being dedicated to one or other of the functions that it has to fulfill. The camera according to the invention advantageously uses a single active zone, which is the same for all the images being captured.

One understands by "camera" any device for acquiring images of the camera type (more particularly the CCD or CMOS type) or sensor, for example a black and white sensor or a color sensor.

In the invention, thus a camera is used, which is already available, that is to say is already used in the vehicle to take images, which are external to the vehicle. This camera is therefore generally focused at infinite, in order to be able, with sufficient clarity, to capture elements, which are external to the vehicle and located at least 20 meters from the latter. This camera thus successfully finds a second application and indeed in a surprising way: One would have thought that a camera focused at infinite, and not focused on the windscreen, would be totally unsuitable for detecting droplets on said windscreen.

Using one camera, instead of two at least, behind the windscreen in the cab interior of the vehicle, allows for greater choice in positioning this camera. However, it is recommended that the field of vision of the camera contains at least one windscreen zone, which is "wipable" by the windscreen wipers of the vehicle under consideration, so that the camera can detect the appearance of new raindrops when the windscreen wipers are stationary and not stagnant droplets.

The camera according to the invention can therefore be disposed in a module level with the vehicle headlining or in proximity thereto, or on the dashboard, in a "gap", for example that of the vehicle instrumentation or that of a navigation screen.

Preferably, the object of the invention is also to create a method for detecting raindrops on a windscreen, and which comprises:

a stage (a) of acquiring images by a camera through the windscreen, camera preferably focused at infinite, a stage (b) of retrieving the contours of the spots present on the acquired images, a stage (c) of realizing the histogram of the widths of contours of the spots.

Indeed, the camera will in fact, taking account of objects on and through the windscreen, in the distance, acquire images each one of which can be considered similar to a group of spots. It has been proven that a spot corresponding to a droplet of water on the windscreen could be distinguished from other spots (corresponding for example to an object of the landscape outside the vehicle) due to its width of contour, which may be quantified by a certain number of pixels. The droplets of water on a windscreen indeed present a contour, which is relatively wider than other spots. Establishing a histogram of these widths of contour makes it possible to select the contour points corresponding to the droplets, then eventually "to reconstruct" these droplets in the images by processing, in order to characterize them finally.

The method according to the invention thus advantageously also comprises:

a stage (d) of thresholding, beyond a given minimum threshold, of the widths of contours of the spots, more particularly in order to confirm the possible presence of spots likely to correspond to droplets on the windscreen.

The method according to the invention also preferably comprises:

a stage (e) of reconstructing the droplets based on the thresholded widths of contour.

at least one stage (f) of characterizing the reconstructed spots, including at least one of the following measurements: measure of variation of the greyscale in the spots, measure of blur of said spots, measure of shape of said spots, count of the number of spots.

Indeed, the study of the morphology of droplets on windscreens has shown that droplets deposited on a surface such as a windscreen had the characteristic of presenting a large variation of greyscale, with a dark zone/light zone transition detectable inside the contours of the spot. It has also been observed that the shape of the contour of the droplet, approximately round, was also a detectable characteristic and particular to the droplets. It has also been noticed that the presence of a droplet in the field of vision of the camera created a blur, which the camera could also pinpoint. Counting the droplets is also useful, in order to be able, more particularly, to distinguish very light rain (not requiring operation of the windscreen wipers to be triggered) from significant rain.

Optionally, the method according to the invention advantageously comprises the introduction of a hierarchical approach, wherein at least one of the stages (b) to (f) is repeated at least once for various image resolutions (full resolution, quarter resolution, eighth resolution, etc.), so as to render the method of detection insensitive to the size of the droplets.

This or these stages (e) and (f) remain optional, the stage of pinpointing the presence of droplets by thresholding the widths of contours being the most distinguishing, and sufficient. These stages of reconstruction and characterization, however, render the possibility of making the results of detection even more reliable, for example by validating the results obtained by the stage of thresholding. They also make it possible to refine the way in which water detection on the windscreen shall be exploited.

For example, if the detection of rain is aimed at triggering the windscreen wipers, simple detection by thresholding the widths of contour is enough to allow the windscreen wipers to be operated fully or not at all. On the other hand, if the method also enables the quantity and shape of the droplets for example to be recognized, operation of the windscreen wipers can be triggered in a more modulated way, in particular with the most suitable wiping speed being selected by modifying the sweeping rate if the conditions change (heavy or light rain).

The method according to the invention also comprises, preferably:

a stage (g) of participating in automatic triggering or automatic modification of a functionality of the vehicle, more particularly actuation of the windscreen wipers, once the droplets of water have been detected on the windscreen or this has been validated.

Naturally, the invention is also interested in the automatic control to stop the windscreen wipers, control which can be triggered when the method for detecting rain according to the invention shows there are no more (or not sufficient) raindrops on the windscreen (because they have been wiped away by the blades of the windscreen wipers, the rain having ceased). The invention can also allow, in particular due to the stage (f) of counting the droplets, the windscreen wipers to be triggered in a modulated way depending on whether the rain is regarded as light (few droplets, moderate sweeping frequency of the windscreen wipers), or heavy (many droplets, heavy rain, increase in the sweeping frequency of the windscreen wipers).

Detecting the presence of rain on the windscreen according to the invention can also be taken into account in further processing of images acquired by the same camera with another aim. It can be a question in particular of detecting images of vehicles driving in the same direction or in the opposite direction, for automatic control of the headlamps, enabling the headlamps to be switched automatically from one operating mode to another. It can be a question, as already suggested, for example of automatically switching the vehicle headlamps from a "full-beam" type state of lighting to a "dipped-beam/sidelight" state of lighting. It can also be a question of detecting the roadside edges, in order to warn the driver if he is involuntarily leaving the roadway (in English, a function called LDWS standing for "Lane Departure Warning Signal").

To increase the reliability of detecting raindrops, it is preferable if stages a of acquisition, b of retrieval, c of realizing the histogram are repeated at least several times, and that their results are compared before triggering, in the event of sufficient consistency, stage g of control, at least ten times for example.

The invention also relates to the device, which enables the method described above to be implemented, with all means adapted to execute all the stages of the latter.

It relates more particularly to a device for detecting raindrops on a windscreen, the device including a camera fitted inside the vehicle, which is opposite the windscreen and which is focused at infinite.

It also relates to a device for detecting raindrops on a windscreen, more particularly according to the preceding claim, which comprises means of acquiring images by a camera through the windscreen, camera more particularly focused at infinite, means of retrieving the contours of the spots present on the acquired images, means of realizing the histogram of the widths of contours of the spots, means of thresholding, beyond a given minimum threshold, of the widths of contours of the spots, in order to confirm the possible presence of spots likely to correspond to droplets on the windscreen, possibly means of reconstructing/characterizing the spots based on the thresholded widths of contour, including at least one means of measuring one of the following parameters: measure of variation of the greyscale in the spots, measure of blur of said spots, measure of shape of said spots, count of said spots.

means of automatic triggering or automatic modification of a functionality of the vehicle, more particularly actuation of the windscreen wipers.

Advantageously the camera used by the device according to the invention is shared with at least one other device equipping said vehicle.

The invention also relates to any means of storing information, memorizing one or more programs, the execution of which authorizes implementation of the method described above.

It also relates to any computer program concerning means of storing information, comprising one or more sequences of executable instructions by a microprocessor and/or a computer, the execution of said sequences of instructions authorizing implementation of the method described above.

Other aspects and advantages of the present invention will become apparent on reading the description of a particular non-limitative mode of embodiment, which relates to the automatic operation of the windscreen wipers when raindrops are detected on the windscreen, written with reference to the appended drawings, wherein:

BRIEF DESCRIPTION OF THE DRAWINGS

FIGS. 3A-3E illustrate the successive stages of processing an image acquired by camera 10 according to the method of the invention.

DESCRIPTION OF THE PREFERRED EMBODIMENTS

These figures are extremely diagrammatic in order to preserve their clarity.

Figure 1:
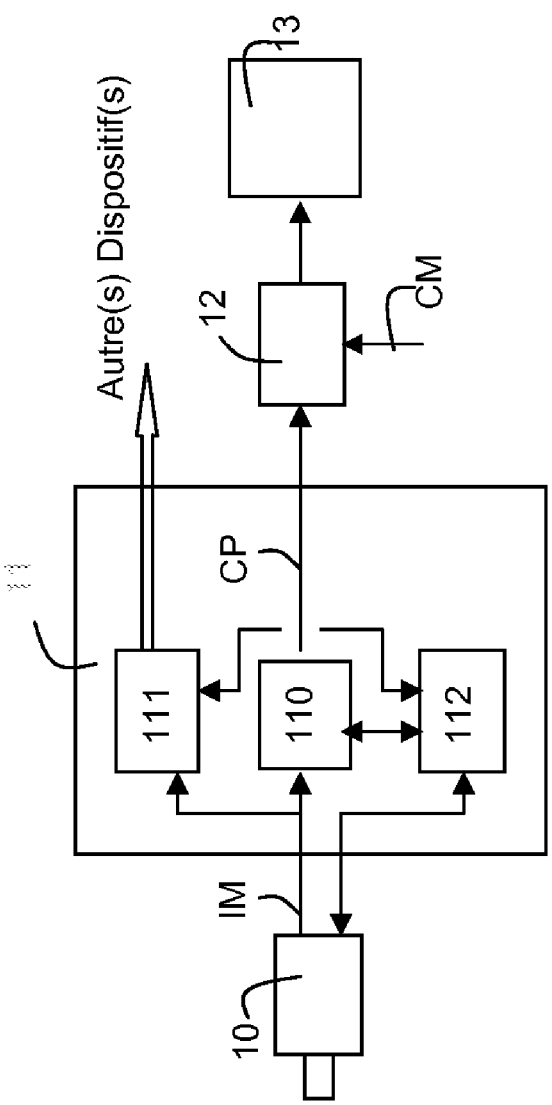
FIG. 1 illustrates the diagrammatic general structure of a windscreen wiper control device using the method for detecting rain according to the invention.

With reference to FIG. 1, the automatic windscreen wiper control device triggers the operation of the windscreen wipers of vehicle 13 when raindrops are detected on the windscreen of a vehicle. It comprises primarily a camera 10, a processing unit 11 and a control circuit 12.

Camera 10 is installed in the cab interior of the vehicle, opposite a "wipable" zone of the windscreen 14, that is to say a zone which is swept by one of the wiper blades while in operation. The camera is fitted for example on the dashboard approximately 30 cm from the windscreen. The camera takes successive images of the road in front of the vehicle through the windscreen. It has a horizontal aperture of approximately 40° and a vertical aperture of approximately 30°. Of course, the position and angular apertures of the camera are shown here by way of simple illustration. Preferably, it is configured so as to have a field of vision of the windscreen measuring at least 20 to 30 $cm^2$, constituting a surface area, which is sufficiently representative of the entire windscreen. Camera 10 delivers images IM to the processing unit 11, more particularly in order to trigger automatic switching of the vehicle headlamps from a "full beam" mode to a "dipped-beam" mode. It will also, as part of the invention, cater for detecting the possible presence of rain on the windscreen.

In the example described here, camera 10 uses a black and white sensor, of suitable dynamics and sensitivity. (It is pointed out that the sensitivity of a sensor corresponds to its capacity to detect weak variations in light intensity and that its dynamics correspond to its capacity to detect over a wide range of light intensities).

Image IM provided by camera 10 is digitized by an analog-to-digital converter (not illustrated) located in the processing unit 11. In the embodiment illustrated in FIG. 1, digitized image IM is fed to processing software modules 110 and 111.

The processing software module 110 is dedicated, in the processing unit 11, to the operation of the control device for the windscreen wipers according to the invention. In accordance with the invention, the processing software module 110 is capable of processing image IM1 and retrieving information CP therefrom for operating windscreen wipers.

The element with the reference symbol 111 schematically illustrates various different processing software modules, located in the processing unit 11, which fulfill processing functions other than those required by the control device for automatically operating the windscreen wiper according to the invention. The software modules 111 belong to other devices, which are fitted in the vehicle and which share images IM and the processing unit 11 with the windscreen wiper control device according to the invention. These other devices for example are a system of road navigational assistance and/or a device for detecting bends to control the headlamps in bends ("bending light" in English) and/or a control device to switch the headlamps from "full-beam" mode to "dipped-beam" mode.

In addition, to the control information CP, control circuit 12 also receives manual control information CM. The manual control information CM is representative of manual operation of the windscreen wipers by the driver of the vehicle. This manual control CM by the driver takes priority over the automatic control CP of the windscreen wipers.

It is not necessary to describe here in detail the architecture of the processing unit, which comprises more particularly a central processing unit such as a microprocessor, a read-only memory, a read-write memory, a storage memory, interfaces and an internal communication bus. In another embodiment of the invention, the processing unit 11 is also equipped with man-machine means of communication, such as a keyboard, with which the driver can select various operating modes. One will also note that the processing unit 11 can take the shape of a programmed apparatus. This programmed apparatus then contains the executable code of the programs in an application-specific integrated circuit (ASIC).

Figure 2:
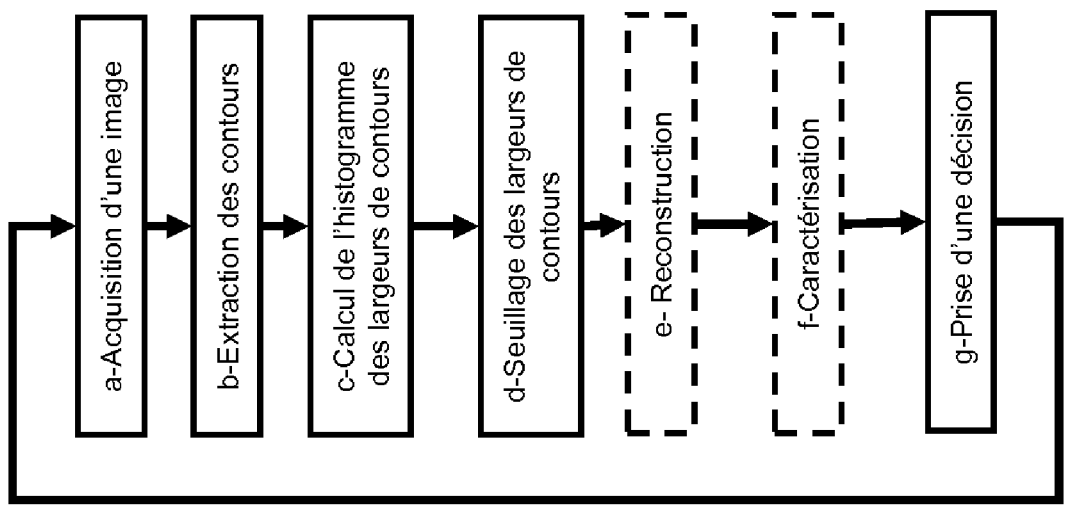
FIG. 2 illustrates an algorithm of an embodiment of a method according to the invention.

FIG. 2 now describes a complete algorithm for a method according to the invention.

The algorithm is broken down in the following way:

stage (a) of acquiring an image by the camera through the windscreen. This is the stage of obtaining an initial image, as shown in FIG. 3A.

stage (b) of retrieving the contours of the spots present on the initial image, and of measuring the width of said contours, operation carried out by a contour recognition operator allowing the width of the contours to be characterized (declivity for example). This is the stage of determining the contours, as shown in FIG. 3B, stage (c) of realizing the histogram of the widths of contours of the spots. This is the stage, which will enable the spots corresponding to raindrops on the windscreen to be distinguished from the other spots of the image. FIG. 3C illustrates such a histogram (X axis being the width of contour in a number of pixels, Y axis being the number of pixels having the width under consideration). It is generally considered that one is dealing with a neat contour when the width of contour is 1 pixel and that the contour is significantly vague beyond 5 pixels, between 5 and 10 pixels for example.

One notices on FIG. 3C a very large number of spots with a width of contour of less than 2 pixels, and a small minority of spots having a width of contour of at least 5 pixels:

stage (d) of thresholding the spots with contour of width of at least 5 pixels. Thus, one identifies the number of spots corresponding to raindrops on the windscreen (or spots likely to correspond to raindrops, if additional stages of validation are envisaged);

stage (e) of reconstructing the droplets (optional): this concerns labelling the droplets located by their width of contour at the time of stage (d) of thresholding: an image processed as illustrated in FIG. 3D is obtained, now containing only the representation of droplets, namely those which can be counted;

stage (f) of characterizing the droplets (optional) following because it uses the data obtained in stage (e) of reconstructing. It consists of performing at least one characterization, for example of the light/dark and dark/light transitions in the spots, (the presence of such transitions being characteristic of raindrops) and/or of counting the droplets. An image as illustrated in FIG. 3E is obtained;

stage (g): triggering of the windscreen wipers if the presence of a sufficient number of droplets is detected (and validated preferably by reiteration, for example at least 10 times, of the previous processing on several successive images to confirm the result). The sensor is capable of taking at least 10 images per second.

In conclusion this type of processing easily enables, in a reliable and reproducible manner in an image taken through a windscreen, raindrops deposited on the windscreen to be distinguished, without requiring a sensor dedicated to detecting rain.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A method comprising the steps of: detecting raindrops on a windscreen, using a camera, which is fitted inside the vehicle opposite the windscreen and which is focused at infinite;
thresholding, beyond a given minimum threshold, of the widths of contours of the spots, more particularly in order to confirm the possible presence of spots likely to correspond to droplets on the windscreen; and
reconstructing the droplets based on the thresholded widths of contour.

2. The method according to claim 1, wherein it uses the camera, which is also used to detect vehicles and roadside edges to make the vehicle headlamps switch from one mode of lighting to another.

3. The method according to claim 1, wherein said method further comprises the step of:
characterizing the reconstructed spots, including at least one of the following measurements: measure of variation of the greyscale in the spots, measure of blur of said spots, measure of shape of said spots, count of the number of spots.

4. The method according to claim 1, wherein at least one of the steps are implemented within the framework of a hierarchical approach.

5. The method according to claim 1, wherein said method further comprises the step of: participating in automatic triggering or automatic modification of a functionality of the vehicle, more particularly actuation of the windscreen wipers, once the droplets of water have been detected on the windscreen.

6. The method according to claim 1 and further comprises the means of storing information, wherein said means memorizes one or more programs, the execution of which authorizes implementation of said method.

7. The method according to claim 1 and further comprises a computer readable medium comprising means of storing information, comprising one or more sequences of executable instructions by a microprocessor executing sequences of instructions authorizing implementation of said method.

8. The method according to claim 1, wherein it uses the camera, which is also used to detect vehicles to make the vehicle headlamps switch from one mode of lighting to another.

9. The method according to claim 1, wherein it uses the camera, which is also used to detect roadside edges to make the vehicle headlamps switch from one mode of lighting to another.

10. The method according to claim 1 and further comprises a computer readable medium comprising means of storing information, comprising one or more sequences of executable instructions by a computer executing sequences of instructions authorizing implementation of said method.

11. The method according to claim 1 and further comprises a computer readable medium comprising means of storing information, comprising one or more sequences of executable instructions by a microprocessor and computer executing sequences of instructions authorizing implementation of said method.

12. A method for detecting raindrops on a windscreen, which comprises the steps of:
a stage (a) of acquiring images by a camera through the windscreen, camera preferably focused at infinite;
a stage (b) of retrieving contours of the spots present on the acquired images;
a stage (c) of realizing a histogram of the widths of said contours of the spots;
a stage (d) thresholding, beyond a given minimum threshold, of the widths of contours of the spots, more particularly in order to confirm the possible presence of spots likely to correspond to droplets on the windscreen; and
a stage (e) of reconstructing the droplets based on the thresholded widths of contour.

13. A device for detecting raindrops on a windscreen, which comprises:
means for acquiring images by a camera through the windscreen, said camera being focused at infinite;
means for retrieving contours of the spots present on the acquired images;
means for realizing the histogram of the widths of contours of the spots;
means for thresholding, beyond a given minimum threshold, of the widths of contours of the spots, in order to identify the possible presence of spots likely to correspond to droplets on the windscreen;
means of reconstructing/characterizing the spots based on the thresholded widths of contour, including at least one means for measuring one of the following parameters: measure of variation of the greyscale in the spots, measure of blur of said spots, measure of shape of said spots, or count of said spots;
means of automatic triggering or automatic modification of a functionality of the vehicle, including at least an actuation of the windscreen wipers.

14. The device according to claim 13, wherein the camera is shared with at least one other device equipping said vehicle.

15. A vehicle rain sensing system for sensing rain on a windshield comprising of: a camera for capturing an image of raindrops and generating information in response thereto; a processor for processing said information and generating contour information of said raindrops; and a control for energizing at least one windshield wiper in response to said contour information;
wherein said processor thresholds beyond a given minimum threshold, of the widths of contours of the spots, more particularly in order to confirm the possible presence of spots likely to correspond to droplets on the windscreen and reconstructs the droplets based on the thresholded widths of contour.

16. The vehicle rain sensing system as claimed in claim 15 wherein said camera is set at infinite focus.

17. The vehicle rain sensing system as claimed in claim 15 in response wherein said processor thereto generates a histogram in response to said raindrops.

18. The vehicle rain sensing system as claimed in claim 17 wherein said histogram is a histogram of widths of raindrops.

19. The vehicle rain sensing system as claimed in claim 15 wherein said camera is adapted to capture images situated away from said windshield.

20. The vehicle rain sensing system as claimed in claim 19 wherein said camera is located in a passenger compartment of said vehicle.

* * * * *